(12) United States Patent
Brenner et al.

(10) Patent No.: US 7,368,265 B2
(45) Date of Patent: May 6, 2008

(54) SELECTIVE GENOME AMPLIFICATION

(75) Inventors: Sydney Brenner, Ely (GB); Gi Mikawa, Cambridge (GB); Stephen C. Macevicz, Cupertino, CA (US)

(73) Assignee: Compass Genetics, LLC, Lutherville, MD (US)

( * ) Notice: Subject to any disclaimer, the term of this patent is extended or adjusted under 35 U.S.C. 154(b) by 0 days.

(21) Appl. No.: 11/656,762

(22) Filed: Jan. 22, 2007

(65) Prior Publication Data

US 2007/0190556 A1 Aug. 16, 2007

Related U.S. Application Data

(60) Provisional application No. 60/761,459, filed on Jan. 23, 2006.

(51) Int. Cl.
C12P 19/34 (2006.01)
(52) U.S. Cl. .................................... 435/91.2
(58) Field of Classification Search ............. 435/91.1, 435/91.2
See application file for complete search history.

(56) References Cited

U.S. PATENT DOCUMENTS

| | | |
|---|---|---|
| 5,130,238 A | 7/1992 | Malek |
| 5,169,766 A | 12/1992 | Schuster |
| 5,194,370 A | 3/1993 | Berninger |
| 5,215,899 A | 6/1993 | Dattagupta |
| 5,399,491 A | 3/1995 | Kacian |
| 5,409,818 A | 4/1995 | Davey |
| 5,437,990 A | 8/1995 | Burg |
| 5,474,916 A | 12/1995 | Reischi |
| 5,545,522 A | 8/1996 | Van Gerlder |
| 5,616,478 A | 4/1997 | Chetverin |
| 5,766,849 A | 6/1998 | McDonough |
| 5,891,636 A | 4/1999 | Van Gelder |
| 5,914,229 A | 6/1999 | Loewy |
| 5,932,451 A | 8/1999 | Wang |
| 6,025,133 A | 2/2000 | Stull |
| 6,132,997 A | 10/2000 | Shannon |
| 6,379,899 B1 | 4/2002 | Ullman |
| 6,403,319 B1 | 6/2002 | Lizardi |
| 6,511,803 B1 | 1/2003 | Church |
| 6,686,156 B2 | 2/2004 | Kurn |
| 6,787,308 B2 | 9/2004 | Balasubramanian |
| 6,794,141 B2 | 9/2004 | Erlander |
| 2003/0165963 A1 | 9/2003 | Liao |
| 2003/0219792 A1 | 11/2003 | Piepenburg |
| 2004/0161792 A1 | 8/2004 | Liao |
| 2005/0112631 A1 | 5/2005 | Piepenburg |
| 2005/0142559 A1 | 6/2005 | Makrgiorgos |
| 2007/0031857 A1* | 2/2007 | Makarov et al. ............. 435/6 |

FOREIGN PATENT DOCUMENTS

| | | |
|---|---|---|
| WO | WO 2004/027025 | 4/2004 |
| WO | WO 2004/076683 | 9/2004 |
| WO | WO 2006081222 | 8/2006 |

OTHER PUBLICATIONS

Kim et al (Biochemical and Biophysical Research Communications, vol. 336, pp. 168-174, 2005.*
Broude, N. Trends in Biotechnology, vol. 20, No. 6, pp. 249-256, 2002.*
Allawi, H.T. & SantaLucia, J., Jr., *Thermodynamics and NMR of internal G.T mismatches in DNA*. Biochemistry 36, 10581-94 (1997).
Becker-Andre et al, *Absolute mRNA quantification using the polymerase chain reaction (PCR). A novel approach by a PCR aided transcript titration assay (PATTY)*.Nucleic Acids Research, 17: 9437-9447 (1989).
Bernard et al, Color multiplexing hybridization probes using the apolipoprotein E locus as a model system for genotyping. Anal. Biochem., 273: 221-228 (1999)(two-color real-time PCR).
Dean et al, *Comprehensive human genome amplification using multiple displacement amplification* Proc. Natl. Acad. Sci., 99: 5261-5266 (2002).
Diviacco et al., *A novel procedure for quantitative polymerase chain reaction by coamplification of competitive templates*.Gene, 122: 313-320 (1992).
Guatelli et al. Isothermal, in vitro amplification of nucleic acids by a multienzyme reaction modeled after retroviral replication. Proc. Natl. Acad. Sci., 87: 1874-1878 (1990).
Hawkins et al, *Whole genome amplification—applications and advances*.Current Opinion in Biotechnology, 13: 65-67 (2002).
Kim et al. DARFA: a novel technique for studying differential gene expression and bacterial comparative genomics. Biochemical and Biophysical Research Communications, 336: 168-174 (2005).
Kwoh. Transcription-based amplification system and detection of amplified human immunodeficiency virus 1 with a bead-based sandwich hybridization format. Proc. Natl. Acad. Sci. 86: 1173-1177 (1989).
Leone et al, *Molecular beacon probes combined with amplification by NASBA enable homogeneous, real-time detection of RNA* Nucleic Acids Research, 26: 2150-2155 (1998).
Mesmaeker et al, *Backbone modifications in oligonucleotides and peptide nucleic acid systems* Current Opinion in Structural Biology, 5: 343-355 (1995).
M. Kanehisa Use of statistical criteria for screening potential homologies in nucleic acid sequences Nucleic Acids Res. 12:203 (1984).

(Continued)

Primary Examiner—Gary Benzion
Assistant Examiner—Cynthia B Wilder
(74) Attorney, Agent, or Firm—David C. Scherer; Carol L. Francis; Bozicevic, Field & Francis LLP (57) ABSTRACT

The invention provides methods and compositions for amplifying selected polynucleotides, especially selected subsets of restriction fragments. Generally, methods of the invention are implemented by ligating adaptors containing at least one promoter sequence to such fragments under conditions that promote the formation of closed single stranded or double stranded structures, which are capable of serving as cyclical templates for transcription.

16 Claims, 5 Drawing Sheets

OTHER PUBLICATIONS

Mackay et al, Real-time PCR in virology Nucleic Acids Research, 30: 1292-1305 (2002).
Margulies et al Genome sequencing in microfabricated high-density picolitre reactors (2005), Nature, 437: 376-380.
Shendure et al, Accurate multiplex polony sequencing of an evolved bacterial genome Science, 309: 1728-1732 (2005).
Xu and Kool, High sequence fidelity in a non-enzymatic DNA autoligation reaction Nucleic Acids Research, 27: 875-881 (1999).

* cited by examiner

pgatctagtgCAGCTTTAATACGACTCACTATAGGGAGAACTAAA*T*
                                                                                         *C*
atcacGTCGAAATTATGCTGAGTGATATCCCTCTTGATT*TT*

SEQUENCE LISTING

<160> NUMBER OF SEQ ID NOS: 5

<210> SEQ ID NO 1
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 1

-continued

```
gatctagtgc agctttaata cgactcacta tagggagaac taaatcttta gttctcccta    60
tagtgagtcg tattaaagct gcacta                                         86
```

<210> SEQ ID NO 2
<211> LENGTH: 172
<212> TYPE: DNA
<213> ORGANISM: Artificial Sequence
<220> FEATURE:
<223> OTHER INFORMATION: Synthetic oligonucleotide

<400> SEQUENCE: 2

```
gatctagtgc agctttaata cgactcacta tagggagaac taaatcttta gttctcccta    60
tagtgagtcg tattaaagct gcactagatc tagtgcagct ttaatacgac tcactatagg   120
gagaactaaa tctttagttc tccctatagt gagtcgtatt aaagctgcac ta           172
```

<210> SEQ ID NO 3
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 3

```
gggaga                                                                6
```

<210> SEQ ID NO 4
<211> LENGTH: 174
<212> TYPE: DNA
<213> ORGANISM: Artificial Sequence
<220> FEATURE:
<223> OTHER INFORMATION: Synthetic oligonucleotide

<400> SEQUENCE: 4

```
gggagaacua aaagauuuag uucucccuau agugagucgu auuaaagcug cacuagaucu    60
agugcagcuu uaauacgacu cacuauaggg agaacuaaaa gauuuaguuc ucccuauagu   120
gagucguauu aaagcugcac uagaucuagu gcagcuuuaa uacgacucac uaua         174
```

<210> SEQ ID NO 5
<211> LENGTH: 522
<212> TYPE: RNA
<213> ORGANISM: Artificial Sequence
<220> FEATURE:
<223> OTHER INFORMATION: Synthetic nucleic acid

<400> SEQUENCE: 5

```
gggagaacua aaagauuuag uucucccuau agugagucgu auuaaagcug cacuagaucu    60
agugcagcuu uaauacgacu cacuauaggg agaacuaaaa gauuuaguuc ucccuauagu   120
gagucguauu aaagcugcac uagaucuagu gcagcuuuaa uacgacucac uauagggaga   180
acuaaaagau uuaguucucc cuauagugag ucguauuaaa gcugcacuag aucuagugca   240
gcuuuaauac gacucacuau agggagaacu aaaagauuua guucucccua uagugagucg   300
uauuaaagcu gcacuagauc uagugcagcu uuaauacgac ucacuauagg gagaacuaaa   360
agauuuaguu cucccuauag ugagucguau uaaagcugca cuagaucuag ugcagcuuua   420
auacgacuca cuauagggag aacuaaaaga uuuaguucuc ccuauaguga gucguauuaa   480
agcugcacua gaucuagugc agcuuuaaua cgacucacua ua                      522
```

SELECTIVE GENOME AMPLIFICATION

CROSS-REFERENCE

This application claims the benefit of U.S. Provisional Application No. 60/761,459 filed Jan. 23, 2006, which application is incorporated herein by reference.

BACKGROUND

The quality and quantity of DNA samples for genetic analysis is critical, e.g. Report of Working Group on Biomedical Technology, "Recommendation for a Human Cancer Genome Project," (February, 2005). A variety of techniques have been developed for amplifying scarce DNA samples, but each involve technical trade-offs so that none is optimal in every circumstance, e.g. Hawkins et al, Current Opinion in Biotechnology, 13: 65-67 (2002); Dean et al, Proc. Natl. Acad. Sci., 99: 5261-5266 (2002). For example, many new DNA sequencing technologies provide tremendous throughput based on short sequence reads, which limits their application to the analysis of relatively small genomes, such as viral and prokaryotic genomes, e.g. Margulies et al, Nature, 437: 376-380 (2005); Shendure et al, Science, 309: 1728-1732 (2005). Many important problems related to mammalian-sized genomes could be amenable to analysis by such technologies, e.g. analysis of cancer genes, if there were available techniques to selectively amplify subsets of large genomes without biases or other deficiencies associated with common amplification techniques.

SUMMARY OF THE INVENTION

The invention provides methods and compositions for amplifying selected polynucleotides, especially selected subsets of restriction fragments. Generally, methods of the invention are implemented by ligating adaptors containing at least one promoter sequence to such fragments under conditions that promote the formation of closed single stranded or double stranded structures, which are capable of serving as cyclical templates for transcription. In one aspect, pairs of hairpin adaptors are ligated to each such fragment, a first hairpin adaptor containing a promoter sequence oriented so that its corresponding RNA polymerase synthesizes transcripts in the direction of the loop region of the hairpin and a second adaptor to provide a return path for the RNA polymerase to cycle back and forth along a fragment being transcribed. Collectively, the pair of hairpin adaptors contain at least one primer binding site so that a primer can be annealed to the transcript for replication by a reverse transcriptase. Preferably, such reverse transcriptase has strand displacement activity so that multiple single stranded DNA copies are produced from each transcript. In another aspect, a single linear adaptor is provided that contains at least one promoter sequence and at least one primer binding site. In accordance with this aspect, such adaptors are ligated to DNA fragments of a selected subset to form DNA circles. Transcription and replication then proceeds as above. Preferably in both aspects, non-closed, i.e. linear, fragments are digested with an exonuclease.

The present invention provides a method of amplifying selected DNA fragments, by ligating to a first end of each DNA fragment a first hairpin adaptor and to a second end of each DNA fragment a second hairpin adaptor to form an augmented sequence, the first and second hairpin adaptors each having a loop region and a duplex region, the duplex region of each first hairpin adaptor containing a promoter sequence oriented so that transcription proceeds toward its loop region, combining the augmented sequence, an RNA polymerase, a reverse transcriptase, a DNA polymerase, and primers specific for one or more primer binding sites within the augmented sequence under reaction conditions such that the RNA polymerase generates transcripts from the augmented sequence, primers anneal to at least one primer binding site and are extended by the reverse transcriptase to produce first complementary DNA strands, primers anneal to first complementary DNA strands and are extended by the DNA polymerase to form second DNA strands, thereby amplifying the selected DNA fragments.

In some embodiments, each hairpin adaptor includes an overhang complementary to an overhang in each DNA fragment. In certain embodiments, the overhang includes at least three nucleotides.

The present invention also provides a method of replicating selected DNA fragments, by providing for each selected DNA fragment an augmented sequence having a first hairpin adaptor at a first end and a second hairpin adaptor at a second end and a selected DNA fragment therebetween, each first hairpin adaptor having a promoter sequence oriented so that synthesis by an RNA polymerase recognizing the promoter sequence proceeds in the direction of the first hairpin adaptor, and each augmented sequence having at least one primer binding site; transcribing the augmented sequence with an RNA polymerase that recognizes the promoter sequence to form an RNA transcript comprising copies of the augmented sequence; generating a complementary DNA from the RNA transcript by annealing a primer to a copy of a strand of the primer binding site and extending it with a reverse transcriptase; generating second DNA strands from complementary DNA strands by annealing a primer to a copy of a strand of the primer binding site and extending it with a DNA polymerase, thereby amplifying the selected DNA fragments.

In some embodiments, each hairpin adaptor includes an overhang complementary to an overhang in each DNA fragment. In certain embodiments, the overhang includes at least three nucleotides.

The present invention also provides a method of amplifying selected DNA fragment by subjecting an augmented nucleic acid sequence and a primer extension mixture to primer extension reaction conditions, the primer extension mixture including an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region, an RNA polymerase, a reverse transcriptase, a DNA polymerase, and primers specific for one or more primer binding sites within the augmented sequence, wherein the RNA polymerase generates transcripts from the augmented sequence, primers anneal to at least one primer binding site and are extended by the reverse transcriptase to produce first complementary DNA strands, primers anneal to first complementary DNA strands and are extended by the DNA polymerase to form second DNA strands, thereby amplifying the selected DNA fragment.

In some embodiments, each hairpin adaptor includes an overhang complementary to an overhang in each DNA fragment. In certain embodiments, the overhang includes at least three nucleotides.

The present invention also provides a method of amplifying selected DNA fragment, by subjecting an augmented nucleic acid sequence and a primer extension mixture to primer extension reaction conditions, the primer extension mixture including: an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region, an RNA polymerase, a reverse transcriptase, and primers specific for one or more primer binding sites within the augmented sequence, wherein the RNA polymerase generates transcripts from the augmented sequence, primers anneal to at least one primer binding site and are extended by the reverse transcriptase to produce first complementary DNA strands, primers anneal to first complementary DNA strands and are extended by the DNA polymerase activity of the reverse transcriptase to form second DNA strands, thereby amplifying the selected DNA fragment.

In some embodiments, each hairpin adaptor includes an overhang complementary to an overhang in each DNA fragment. In certain embodiments, the overhang includes at least three nucleotides.

The present invention also provides a reaction mixture, including an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region, and primers specific for one or more primer binding sites within the augmented sequence.

In some embodiments, the reaction mixture further includes an RNA polymerase, a reverse transcriptase, or a DNA polymerase. In some embodiments, each hairpin adaptor includes an overhang complementary to an overhang in each DNA fragment. In certain embodiments, the overhang includes at least three nucleotides.

The present invention also provides a reaction mixture for use in a process for the amplification a selected DNA fragment, including an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region; an RNA polymerase; a reverse transcriptase; a DNA polymerase; and primers specific for one or more primer binding sites within the augmented sequence.

In some embodiments, each hairpin adaptor includes an overhang complementary to an overhang in each DNA fragment. In certain embodiments, the overhang includes at least three nucleotides.

The present invention also provides a reaction mixture for use in a process for the amplification a selected DNA fragment, including an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region; an RNA polymerase; a reverse transcriptase; and primers specific for one or more primer binding sites within the augmented sequence.

In some embodiments, each hairpin adaptor includes an overhang complementary to an overhang in each DNA fragment. In certain embodiments, the overhang includes at least three nucleotides.

These and other objects, advantages, and features of the invention will become apparent to those persons skilled in the art upon reading the details of the invention as more fully described below.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 3 shows an exemplary amplification using the described hairpin adaptors. The template sequence is shown in uppercase typeface (SEQ ID NO:02), with the T7 promoter sequence in bold and boxed typeface, followed by leader sequence GGGAGA (SEQ ID NO:03) in bold typeface. The 4 base overhang sequence used for combining two looped DNA is in indicated in double underline typeface. The 3 base loops on both ends are indicated in italics typeface. One unit length of transcript is shown in lowercase typeface (SEQ ID NO:04), with a concatenated transcript below (SEQ ID NO:05). Capture primer annealing sites in the concatenated transcript are represented in boxes and primer extension direction is indicated by arrow. As a result, the amplification fold is multiplied by the copy number of concatenated RNA molecules.

DEFINITIONS

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually but not necessarily double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. "RNA amplicon" means an amplicon of RNA molecules; that is, starting sequences, which may be RNA or DNA, give rise to RNA replicates in an amplicon.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a gene or portion of a gene in a genome, or it may refer to any contiguous portion of genomic sequence whether or not it is within, or associated with, a gene. Preferably, a genetic locus refers to any portion of genomic sequence from a few tens of nucleotides, e.g. 10-30, or 10-100, in length, to a few hundred nucleotides, e.g. 100-1000 or 100-500 in length, to a few thousands of nucleotide in length, e.g. 1000-10,000 or 1000-3000 in length. In some contexts, genetic locus may refer to the location of a nucleotide within a genome.

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Mutation" and "polymorphism" are usually used somewhat interchangeably to mean a DNA molecule, such as a gene, that differs in nucleotide sequence from a reference DNA sequence, or wild type sequence, or normal tissue sequence, by one or more bases, insertions, and/or deletions. In some contexts, the usage of Cotton (Mutation Detection, Oxford University Press, Oxford, 1997) is followed in that a mutation is understood to be any base change whether pathological to an organism or not, whereas a polymorphism is usually understood to be a base change with no direct pathological consequences.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like. A readout is "digital" when the number or value is obtained by a counting process, e.g. determining a value by counting on a microarray the number of hybridization from which signals are being generated (as distinguished from those sites not generating signals).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. $Tm=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Vector" or "cloning vector" refers to an extrachromosomal genetic element which can be used to replicate a DNA fragment in a host organism. A wide variety of cloning vectors are commercially available for use with the invention, e.g. New England Biolabs (Beverely, Mass.); Stratagene Cloning Systems (La Jolla, Calif.); Clontech Laboratories (Palo Alto, Calif.); and the like. Usually, cloning vectors used with the invention are bacterial plasmids.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention provides a method for amplifying, or replicating, selected subsets of polynucleotides in a reaction. In one aspect of the invention, such subsets of polynucleotides are subsets of restriction fragment generated by digesting one or more genomes, such as mammalian genomes, with one or more restriction endonucleases.

Preferably, such digestions are carried out with pairs of restriction endonucleases wherein one member of the pair is a rare cutter, for example, having a recognition sequence of seven or more nucleotides, and the other member of the pair is a frequent cutter, for example having a recognition sequence of six or fewer nucleotide, and usually, of four nucleotides. Exemplary rare cutter restriction endonucleases include, but are not limited to, Aar I, Asc I, AsiS I, BbvC I, Fse I, Not I, Rsr II, SanD I, Sap I, and the like. Exemplary, frequent cutter restriction endonucleases include, but are not limited to, Tsp509 I, Fat I, Dpn II, Mbe I, Sau3A I, BssK I, StyD4 I, Dde I, Sau96 I, Fmu I, and the like. In order to minimize or prevent undesired self ligations or concatenations, preferably restriction endonucleases are employed that leave three-base overhangs, or that leave four-base overhangs that can be filled-in by one base in a polymerase extension reaction to produce a three-base overhang.

The method of the invention is based in part on the discovery that RNA polymerases recognizing a promoter oriented to promote synthesis in the direction of a hairpin loop are able to synthesize an RNA transcript across the loop and along the complementary strand containing the promoter sequence itself. This discovery is exploited in one aspect of the invention illustrated in FIG. 1A. Genomic DNA (100) is digested with, for example, two restriction endonucleases to produce (104) DNA fragments (105) containing a subset in which each fragment has two non-complementary overhangs, referred to herein as "asymmetric fragments." To each asymmetric fragment (102) is ligated first hairpin adaptor (106) and second hairpin adaptor (114) to form closed single stranded DNA (122) containing large self-complementary region (123). First hairpin adaptor (106) comprises duplex region (110) and loop region (108). Within duplex region (110) first hairpin adaptor (106) contains promoter sequence (112) oriented so that an RNA polymerase recognizing such sequence synthesizes a transcript in the direction of loop region (108).

Figure 1A:
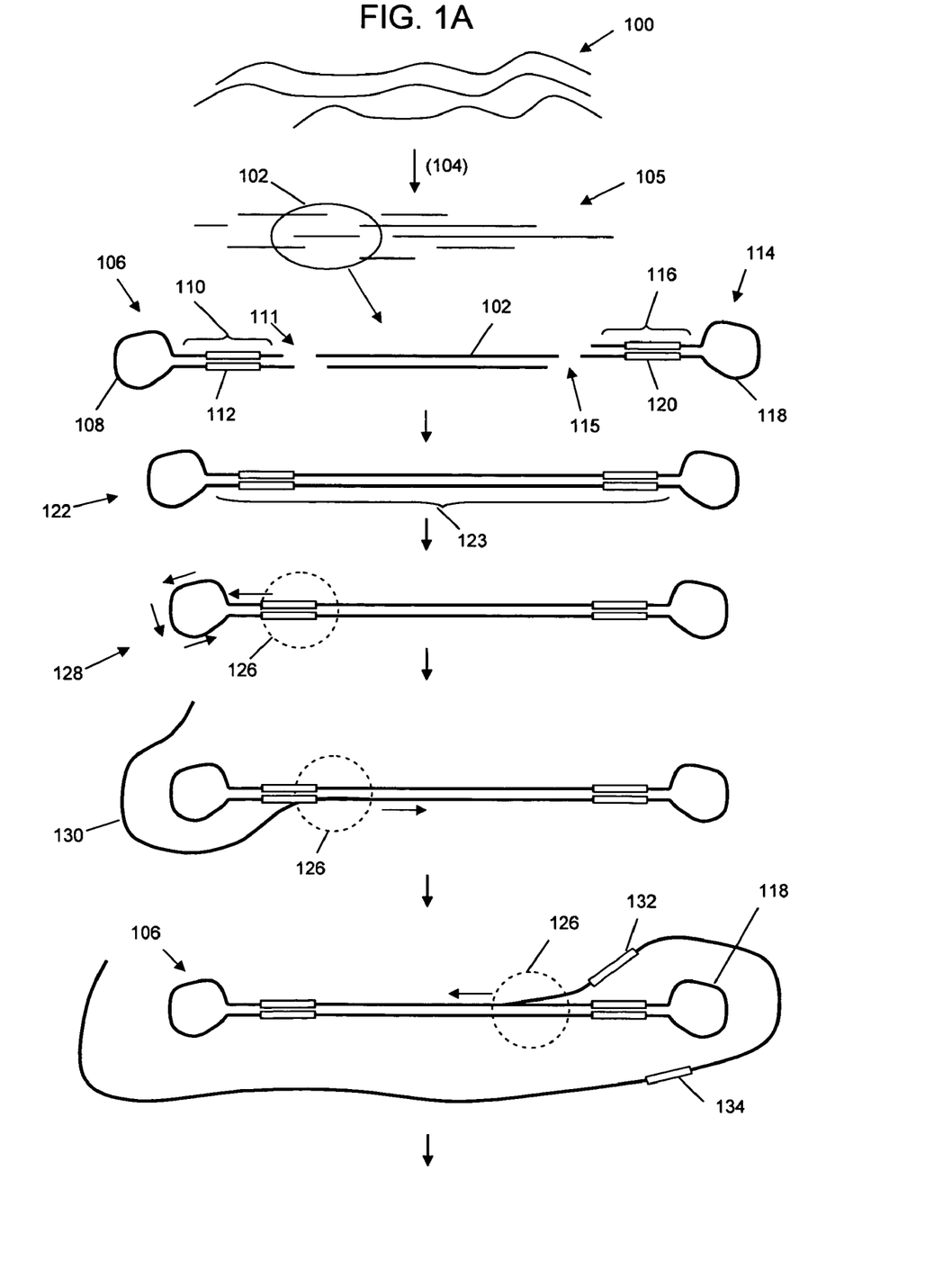
FIGS. 1A-1C diagrammatically illustrate steps of several embodiments of the invention.
Figure 1B:
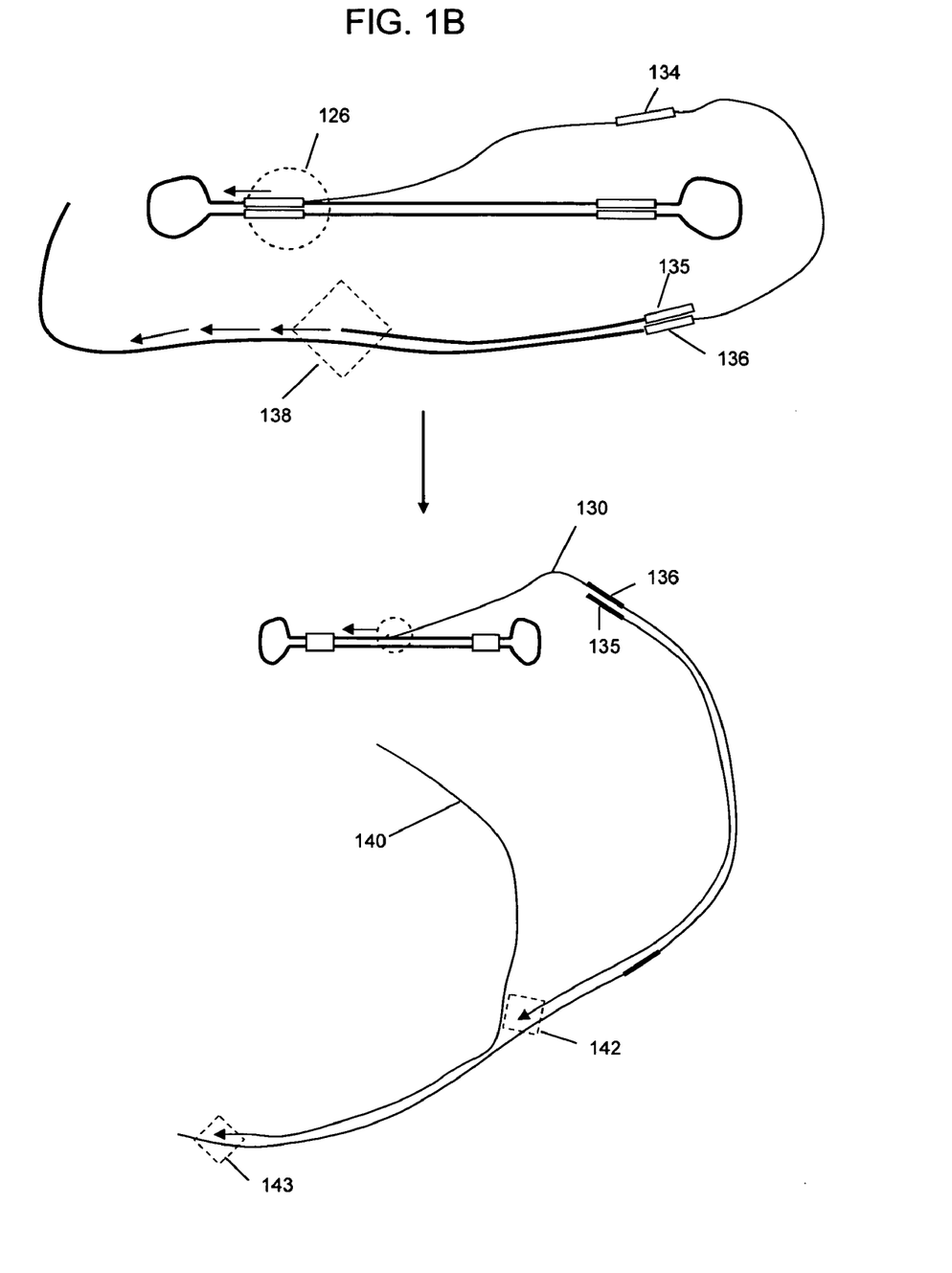

In some embodiments, first hairpin adaptor (106) has an overhang complementary to an overhang of DNA fragment (102). The overhang can range from about 2 nucleotides to about 6 nucleotides, including about 3 nucleotides or 4 nucleotides. Second hairpin adaptor (114) comprises duplex region (116) and loop region (118), and preferably within duplex region (116) second hairpin adaptor (114) contains primer binding site (120). As above, in some embodiments, the second hairpin adaptor (114) has an overhang complementary to an overhang of DNA fragment (102). The overhang can range from about 2 nucleotides to about 6 nucleotides, including about 3 nucleotides or 4 nucleotides. After formation of closed single stranded DNA (122), RNA polymerase (126) recognizing promoter sequence (112) is able to synthesize (128) transcript (130) over loop region (108) and back in the direction of second hairpin adaptor (114). Upon reaching second hairpin adaptor (114), RNA polymerase (126) continues to synthesize transcript (130) through loop region (118) and along fragment (102) back towards first hairpin adaptor (106). In the process of such synthesis, replicates are made of both strands, (132) and (134), of primer binding site (120). As a result, the amplification fold is multiplied by the copy number of concatenated RNA molecules.

For amplification beyond that solely provided by the continuous transcription process, primer (135) anneals to site (136) (or (134)) and is extended by reverse transcriptase (138). Preferably, reverse transcriptase (138) is selected that have strand displacement activity so that as strand (140) is synthesized by reverse transcriptase (143) its 5' end is displaced from transcript (130) by reverse transcriptases (142) that initiate synthesis from successively produced primer binding sites (136) of transcript (130). Amplification can be increased further by action of a DNA polymerase selected to use single stranded DNA (140), and like strands, as templates, in a manner analogous to whole genome amplification using phi29 DNA polymerase, described by Dean et al, Genome Research, 11: 1095-1099 (2001). Amplification employing strand displacement activity of polymerases is also disclosed in Dean et al, U.S. Pat. No. 6,617,137 and Lizardi et al, U.S. Pat. No. 6,124,120, which are incorporated by references.

Figure 1C:
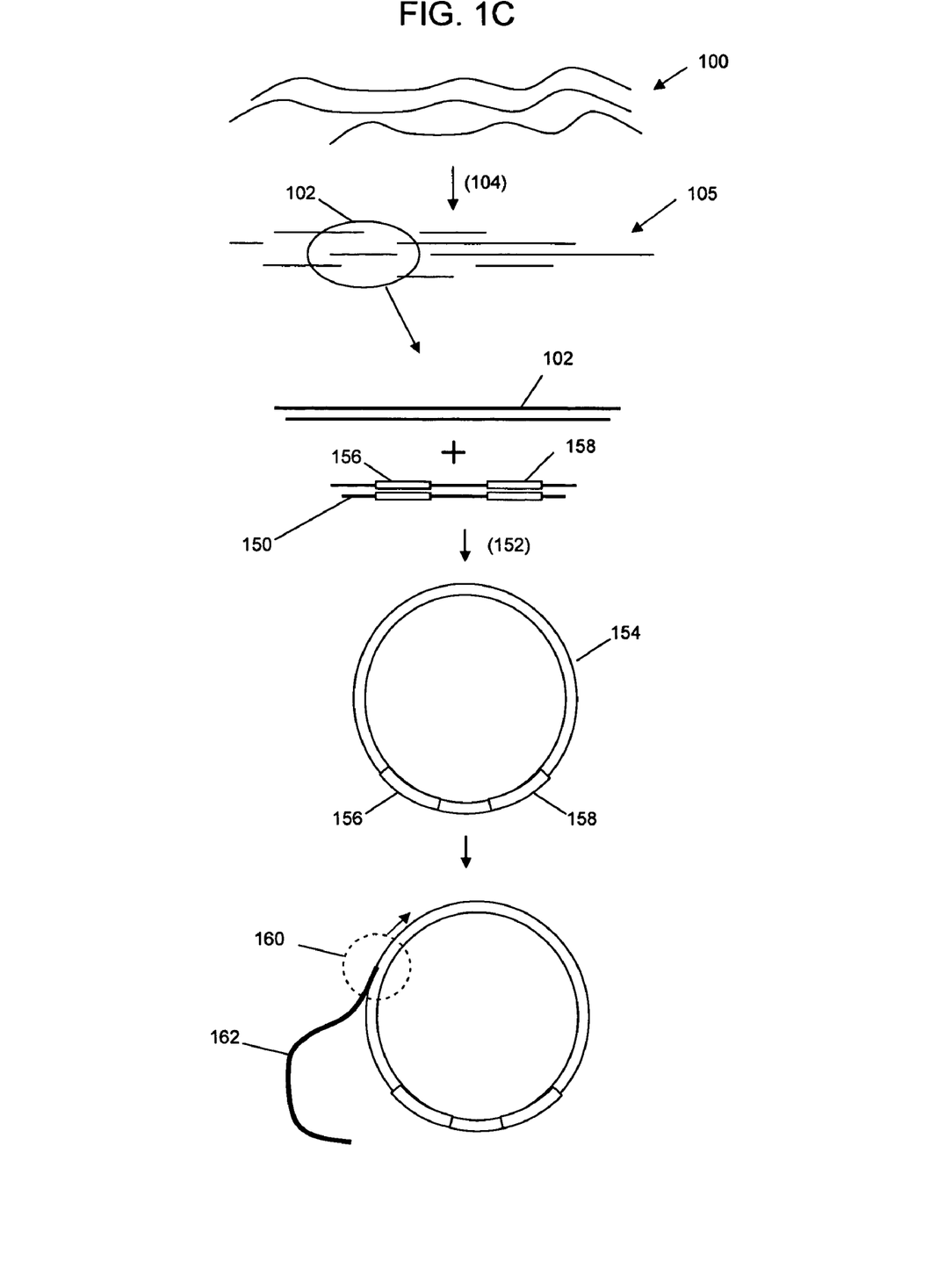

In another aspect, the invention employs the formation of double stranded DNA circles for selective amplification, as illustrated in FIG. 1C. Genomic DNA (100) is prepared similarly as described above to form (104) DNA fragments (105). Preferably, to each asymmetric fragment (102) is ligated under circle-forming conditions linear adaptor (150) having complementary ends to fragment (102). Linear adaptor (150) contains at least one promoter sequence (156) and at least one primer binding site (158). After formation (152) of double stranded DNA circles (154), preferably nucleic acids remaining in a linear state are digested with an exonuclease. Whether or not an exonuclease is employed, double stranded DNA circles (154) are treated with RNA polymerase (160) to produce transcript (162). As above, transcript (162) can be further amplified by adding under extension reaction conditions primers specific for either strand of primer binding site (158), a reverse transcriptase, and a DNA polymerase.

Reaction Mixture

Generally, the reaction mixtures include (i) an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region, and (ii) primers specific for one or more primer binding sites within the augmented sequence. In certain embodiments, the reaction mixture further includes an RNA polymerase, a reverse transcriptase, and a DNA polymerase.

In some embodiments, in addition to the above components, the reaction mixture may further include template nucleic acid and deoxyribonucleoside triphosphates (dNTPs). Usually the primer extension reaction mixture will comprise four different types of dNTPs corresponding to the four naturally occurring bases are present, i.e. dATP, dTTP, dCTP and dGTP. In the subject methods, each dNTP will typically be present in an amount ranging from about 10 to 5000 µM, usually from about 20 to 1000 µM.

The reaction mixture may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture, the various constituent components may be combined in any convenient order. For example, the buffer may be combined with the primers, RNA polymerase, reverse transcriptase and DNA polymerase and then the augmented nucleic acid, or all of the various constituent components may be combined at the same time to produce the reaction mixture.

The following example is put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE

Figure 2:
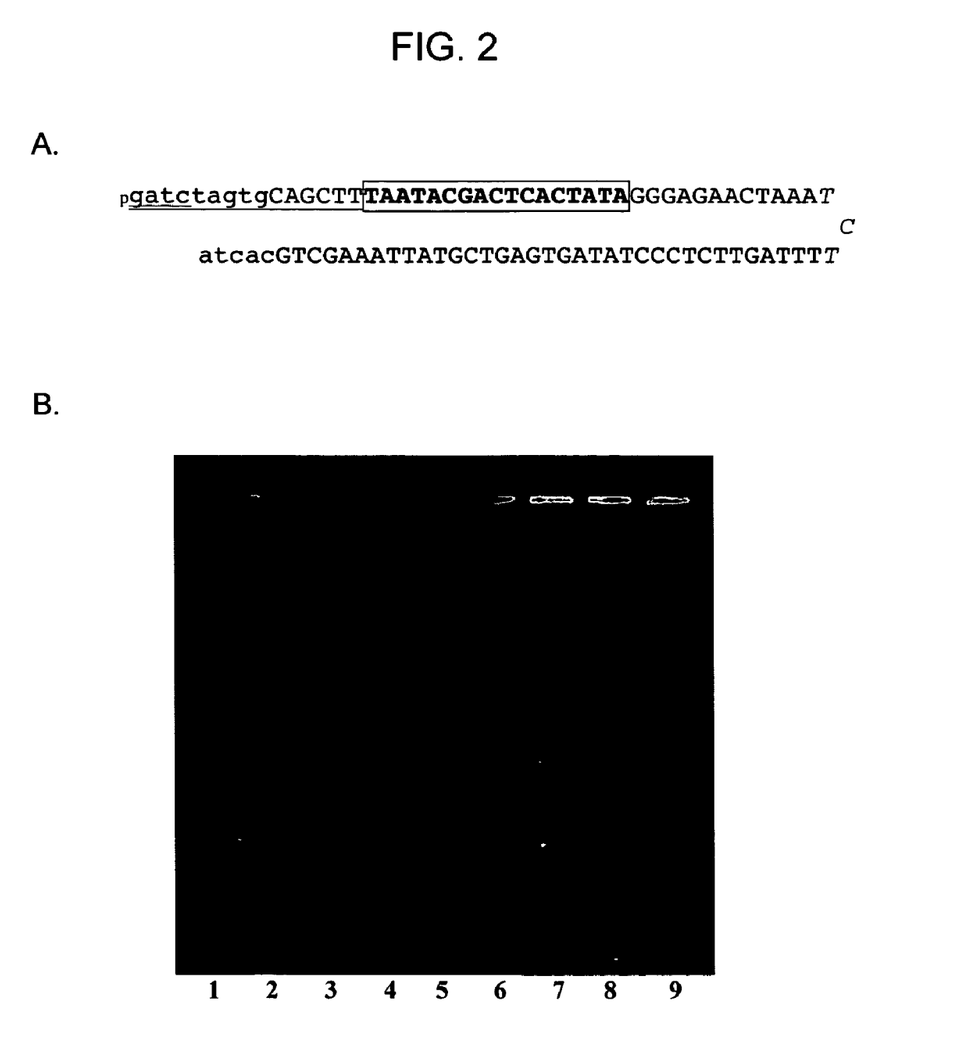
FIG. 2 shows amplification from template DNA. Panel A shows the sequence of an exemplary hairpin adaptor (SEQ ID NO:01). The three nucleotide loop is indicated in italics typeface, the T7 promoter with a transcription direction facing towards the loop is indicated in bold and boxed typeface, the capture primer sequence is indicated un underlined typeface, and the overhang sequence is depicted in double underlined typeface. Panel B is a gel showing the amplification pattern. Lanes 2 through 5 show the amplification reaction from non-ligated template. Lanes 6 through 9 show amplification from dumbbell shaped template.

An example of selective amplification was carried out using two hairpin adaptor sequences self ligated to each other. Panel A of FIG. 2 shows the sequence of single hairpin adaptor. The dumbbell shaped DNA for the assay was generating by ligating two hairpin adaptors at the GATC sequence. The three nucleotide loop is indicated in italics typeface, the T7 promoter with a transcription direction facing towards the loop is indicated in bold and boxed typeface, the capture primer sequence is indicated un underlined typeface, and the overhand sequence is depicted in double underline typeface.

Figure 3:
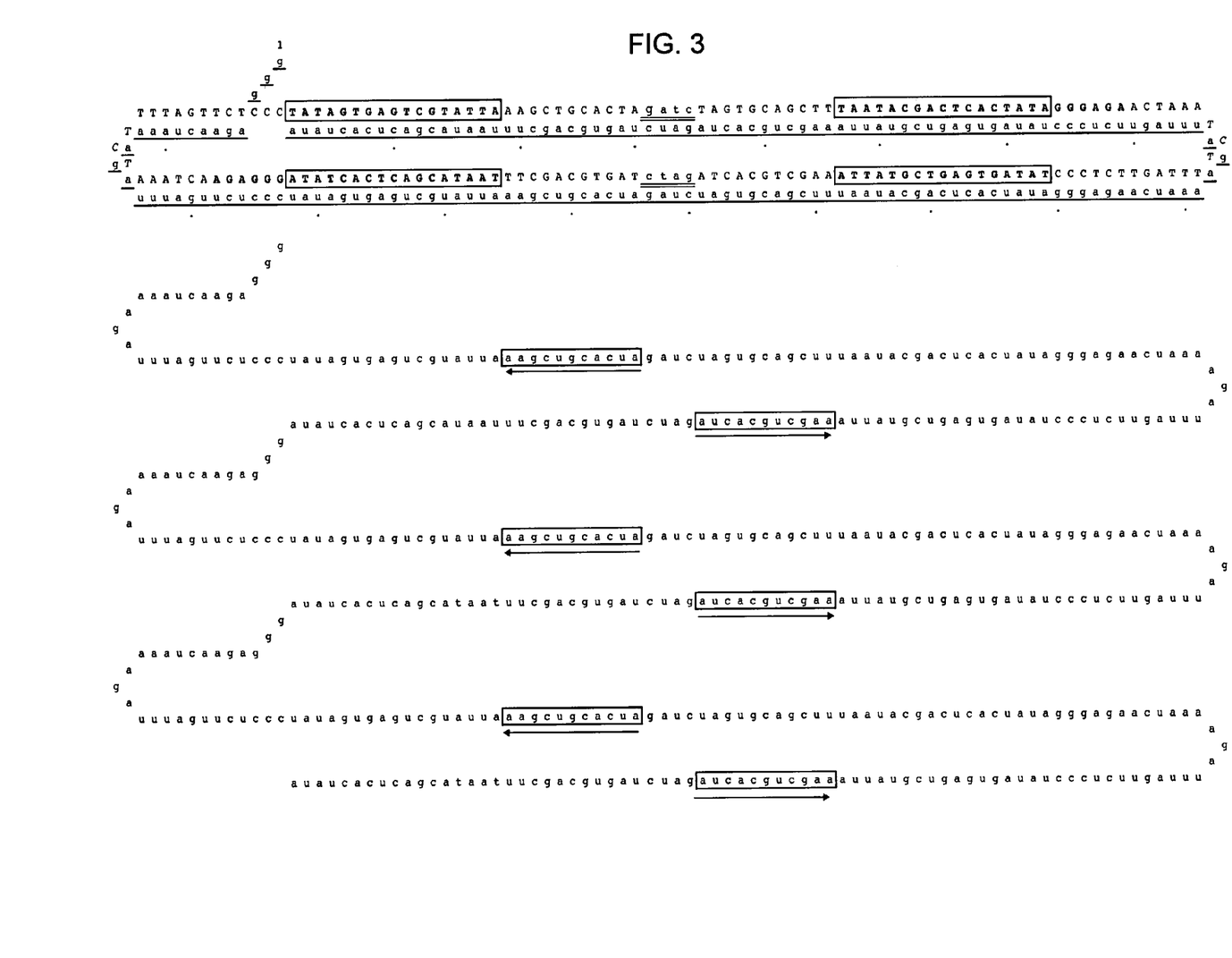

FIG. 3 shows a schematic amplification using the self-ligated hairpin adaptors. The template sequence is shown in uppercase typeface, with the T7 promoter sequence in bold and boxed typeface, followed by leader sequence GGGAGA (SEQ ID NO:03) in bold typeface. The 4 base overhang sequence used for combining two looped DNA is in indicated in double underline typeface. The 3 base loops on both ends are indicated in italics typeface. One unit length of transcript is shown in lowercase typeface, with a concatenated transcript below. Capture primer annealing sites in the concatenated transcript are represented in boxes and primer extension direction is indicated by arrow. As a result, the amplification fold is multiplied by the copy number of concatenated RNA molecules.

Amplification pattern form the dumbbell shaped DNA is shown in FIG. 2, panel B. from the Panel B is a gel showing the amplification pattern. The contents of each reaction mixture in each lane are provided in detail in Table 1. Lanes 2 through 5 show the amplification reactions from non-ligated hairpin adaptors with various units of T7 Exo. Lanes 6 through 9 show amplification from the dumbbell shaped template formed from ligation of two hairpin adaptor sequences with various units of T7 Exo.

TABLE 1

| | Lane | | | | | | | |
|---|---|---|---|---|---|---|---|---|
| | 2 | 3 | 4 | 5 | 6 | 7 | 8 | 9 |
| Template | I | I | I | I | DB | DB | DB | DB |
| Seq | + | + | + | + | + | + | + | + |
| RT | + | + | + | + | + | + | + | + |
| T7RNAP | + | + | + | + | + | + | + | + |
| T7Exo (U) | 0 | 4 | 6 | 8 | 0 | 4 | 6 | 8 |

I = template I,
DB = self ligated template I.
Lane 2 to 5 show the size of one unit length of cDNA synthesized from the transcript transcribed from template I. Lane 6 to 9 show the concatenated cDNA synthesized from the transcript transcribed from the dumbbell shaped template.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of amplifying selected DNA fragments, the method comprising the steps of:
    ligating to a first end of each DNA fragment a first hairpin adaptor and to a second end of each DNA fragment a second hairpin adaptor to form an augmented sequence, the first and second hairpin adaptors each having a loop region and a duplex region, the duplex region of each first hairpin adaptor containing a promoter sequence oriented so that transcription proceeds toward its loop region;
    combining the augmented sequence, an RNA polymerase, a reverse transcriptase, a DNA polymerase, and primers specific for one or more primer binding sites within the augmented sequence under reaction conditions such that the RNA polymerase generates transcripts from the augmented sequence, primers anneal to at least one primer binding site and are extended by the reverse transcriptase to produce first complementary DNA strands, primers anneal to first complementary DNA strands and are extended by the DNA polymerase to form second DNA strands, thereby amplifying the selected DNA fragments.

2. The method of claim 1, wherein the each hairpin adaptor comprises an overhang complementary to an overhang in each DNA fragment.

3. The method of claim 2, wherein the overhang comprises at least three nucleotides.

4. A method of replicating selected DNA fragments, the method comprising the steps of:
    providing for each selected DNA fragment an augmented sequence having a first hairpin adaptor at a first end and a second hairpin adaptor at a second end and a selected DNA fragment there between, each first hairpin adaptor having a promoter sequence oriented so that synthesis by an RNA polymerase recognizing the promoter sequence proceeds in the direction of the first hairpin adaptor, and each augmented sequence having at least one primer binding site;
    transcribing the augmented sequence with an RNA polymerase that recognizes the promoter sequence to form an RNA transcript comprising copies of the augmented sequence;
    generating a complementary DNA from the RNA transcript by annealing a primer to a copy of a strand of the primer binding site and extending it with a reverse transcriptase;
    generating second DNA strands from complementary DNA strands by annealing a primer to a copy of a strand of the primer binding site and extending it with a DNA polymerase, thereby amplifying the selected DNA fragments.

5. The method of claim 4, wherein the each hairpin adaptor comprises an overhang complementary to an overhang in each DNA fragment.

6. The method of claim 5, wherein the overhang comprises at least three nucleotides.

7. A method of amplifying selected DNA fragment, the method comprising the steps of:
    subjecting an augmented nucleic acid sequence and a primer extension mixture to primer extension reaction conditions, the primer extension mixture comprising:
        an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region,
        an RNA polymerase,
        a reverse transcriptase,
        a DNA polymerase, and
        primers specific for one or more primer binding sites within the augmented sequence,
    wherein the RNA polymerase generates transcripts from the augmented sequence, primers anneal to at least one primer binding site and are extended by the reverse transcriptase to produce first complementary DNA strands, primers anneal to first complementary DNA strands and are extended by the DNA polymerase to form second DNA strands, thereby amplifying the selected DNA fragment.

8. The method of claim 7, wherein the each hairpin adaptor comprises an overhang complementary to an overhang in each DNA fragment.

9. The method of claim 8, wherein the overhang comprises at least three nucleotides.

10. A method of amplifying selected DNA fragment, the method comprising the steps of:
    subjecting an augmented nucleic acid sequence and a primer extension mixture to primer extension reaction conditions, the primer extension mixture comprising:
        an augmented nucleic acid sequence comprising a DNA fragment having a first hairpin adaptor ligated to the first end of the DNA fragment and a second hairpin adaptor ligated to the second end of the DNA fragment, wherein the first and second hairpin adaptors have a loop region and a duplex region, and wherein the duplex region of the first hairpin adaptor comprises a promoter sequence oriented so that transcription proceeds toward the loop region,
        an RNA polymerase,
        a reverse transcriptase, and
        primers specific for one or more primer binding sites within the augmented sequence,
    wherein the RNA polymerase generates transcripts from the augmented sequence, primers anneal to at least one primer binding site and are extended by the reverse transcriptase to produce first complementary DNA strands, primers anneal to first complementary DNA strands and are extended by the DNA polymerase activity of the reverse transcriptase to form second DNA strands, thereby amplifying the selected DNA fragment.

11. The method of claim 10, wherein the each hairpin adaptor comprises an overhang complementary to an overhang in each DNA fragment.

12. The method of claim 11, wherein the overhang comprises at least three nucleotides.

13. The method of claim 1, wherein the augmented sequence is a closed single stranded DNA.

14. The method of claim 4, wherein the augmented sequence is a closed single stranded DNA.

15. The method of claim 7, wherein the augmented sequence is a closed single stranded DNA.

16. The method of claim 10, wherein the augmented sequence is a closed single stranded DNA.

* * * * *